US007892202B2

(12) United States Patent
Lampropoulos et al.

(10) Patent No.: US 7,892,202 B2
(45) Date of Patent: Feb. 22, 2011

(54) SYSTEM AND METHOD FOR INFLATION SYRINGE WITH IMPROVED DISPLAY

(75) Inventors: Fred P. Lampropoulos, Salt Lake City, UT (US); Steve Taylor, Salt Lake City, UT (US); Thomas Stout, Salt Lake City, UT (US); Jim Mottola, Salt Lake City, UT (US); Blaine Johnson, Riverton, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 113 days.

(21) Appl. No.: 12/118,442

(22) Filed: May 9, 2008

(65) Prior Publication Data

US 2009/0281489 A1 Nov. 12, 2009

(51) Int. Cl.
*A61M 29/00* (2006.01)
(52) U.S. Cl. .............. 604/100.03; 604/100.01; 604/121; 604/97.03; 604/246; 604/218; 604/187; 604/181; 604/118; 604/38
(58) Field of Classification Search .............. 604/97.03, 604/98.01, 100.01–100.03, 187, 218, 246, 604/118, 181, 38, 121
See application file for complete search history.

(56) References Cited

U.S. PATENT DOCUMENTS

| | | | |
|---|---|---|---|
| 4,370,982 A | | 2/1983 | Reilly |
| 4,841,977 A | | 6/1989 | Griffith et al. |
| 5,084,060 A | | 1/1992 | Freund et al. |
| 5,135,488 A | * | 8/1992 | Foote et al. .............. 604/97.03 |
| 5,284,480 A | * | 2/1994 | Porter et al. .............. 604/97.03 |
| 5,449,345 A | * | 9/1995 | Taylor et al. ........... 604/100.03 |
| 5,562,621 A | * | 10/1996 | Claude et al. .......... 604/100.03 |
| 5,749,853 A | * | 5/1998 | O'Donnell et al. ....... 604/97.03 |
| 6,394,977 B1 | | 5/2002 | Taylor et al. |

(Continued)

FOREIGN PATENT DOCUMENTS

WO 2009/040310 4/2009

(Continued)

OTHER PUBLICATIONS

International Search Report for PCT/US2009/040310.

(Continued)

*Primary Examiner*—Nicholas D Lucchesi
*Assistant Examiner*—Leah Stohr
(74) *Attorney, Agent, or Firm*—Stoel Rives LLP

(57) ABSTRACT

An inflation syringe having an improved display and method of displaying pressurization information. More particularly, the present invention relates to methods and apparatuses for providing both numeric and non-numeric indications of an inflation pressurization associated with an inflation syringe. According to one embodiment of the present invention, a progressive non-numeric display is provided for displaying the pressurization of the inflation syringe along with numeric indicators of the pressurization. The progressive display includes a plurality of indicia corresponding to a range of inflation pressurization values. The indicia are actuated to indicate inflation pressurization and to allow the practitioner to not only easily monitor the general intensity of the pressurization but to monitor changes in the pressurization without needing to interpret numerical values. This permits the user to ascertain the relationship between the current pressurization, desired pressurization, and the rate of pressurization.

26 Claims, 9 Drawing Sheets

U.S. PATENT DOCUMENTS

| | | |
|---|---|---|
| 6,533,757 B1 * | 3/2003 | Lampropoulos et al. .... 604/131 |
| 7,051,594 B1 | 5/2006 | Aziz |
| D597,037 S | 7/2009 | Lampropoulos et al. |
| 2002/0045854 A1 * | 4/2002 | Royo et al. .............. 604/97.03 |

FOREIGN PATENT DOCUMENTS

| | | |
|---|---|---|
| WO | 2009/068058 | 12/2009 |

OTHER PUBLICATIONS

U.S. Appl. No. 12/638,631, filed Dec. 5, 2009, Lampropoulos et al.

* cited by examiner

SYSTEM AND METHOD FOR INFLATION SYRINGE WITH IMPROVED DISPLAY

BACKGROUND OF THE INVENTION

1. Field of the Invention

Exemplary embodiments of the present invention relates to an inflation device that is used for controlling the inflation of a balloon-tipped catheter. In more particular, the present invention relates to an improved inflation data display that provides an intuitive numeric and non-numeric representation of the inflation pressurization values to facilitate improved monitoring of balloon catheter inflation pressures. The present invention also relates to an improved modularized component assembly system for facilitating assembly of the inflation device apparatus.

2. Relevant Technology

Inflation syringes and catheter technologies have become increasingly important in the interventional radiology and cardiology medical fields. Balloon-tipped catheter systems and inflation syringe apparatus have been utilized in various fields of medicine, such as urology, gynecology, cardiology and others. One area in which balloon-tipped catheter systems and their associated syringe systems have resulted in significant improvement over traditional treatment methods is in connection with the treatment of coronary artery disease.

Coronary artery disease and the associated narrowing of the arteries that feed oxygen-rich blood to the heart (a condition known as "stenosis") is one of the conditions for which balloon-tipped catheters are often utilized as a method of treatment. Traditionally, coronary artery blockages were treated with medicine or by performing coronary artery by-pass surgery. Various kinds of medication could be administered which would decrease the work of the heart by slowing the heart rate, dilating the blood vessels, or lowering blood pressure. However, such medicinal treatments did not cure coronary artery narrowing. As a result, not only would the arterial narrowing remain, but it would also continue to present a risk that at some point the narrowing would become serious enough to require surgical intervention.

In coronary artery by-pass surgery, a blood vessel from the chest or leg is grafted by passing the point of blockage so that the blood detours past the blockage in order to reach the heart. In some severe cases, multiple by-passes are performed. As is well known, coronary artery by-pass surgery is an expensive, highly invasive procedure which often requires prolonged hospitalization and recovery periods.

In the last several years, another method for treating coronary artery disease has developed, called balloon coronary angioplasty, or more technically, percutaneous transluminal coronary angioplasty (PTCA). PTCA is a much less traumatic procedure than coronary artery by-pass surgery. PTCA takes about two hours to perform and can be conducted under local anesthesia. PTCA has significantly improved patient recovery times allowing patients to resume normal activities in a matter of days. Because PTCA is much less expensive and less traumatic than by-pass surgery while still providing effective blockage removal, PTCA has experienced a dramatic increase in the number of such procedures performed each year.

To perform a typical PTCA procedure, an introducer sheath is inserted through an incision made in the groin of the patient or in the artery of an arm of the patient. An x-ray sensitive dye is injected into the coronary artery through a catheter that is introduced through the sheath. The dye enables the doctor, through the use of real-time x-ray technology, to clearly view the patient's vasculature on a television monitor and to thereby locate the blockage. A balloon-tipped catheter is advanced through the vasculature to the point of the blockage with the help of the x-ray monitor.

Due to the increase in the number of PTCA procedures being performed, there has been a substantial increase in the use of electronically monitored inflation syringe systems which are utilized to inflate the balloon catheter or other inflatable balloon-type device during PTCA procedures. Typical syringe systems comprise a barrel and a plunger which are selectively operable to increase fluid pressure applied to the balloon catheter and to remove the applied pressure to the balloon catheter once the procedure is finished. The syringe systems are adapted to provide user readable feedback to the practitioner in the form of a numeric value allowing the practitioner to assess the amount of pressurization that is being applied to the balloon. This allows the practitioner to closely monitor pressurization values to provide a more controlled and systematic inflation of the balloon during the procedure.

Many of the apparatus utilized in PTCA procedures are inexpensive devices which can be discarded after a single use. Disposable devices eliminate expensive and time consuming sterilization procedures which are necessary for reusable devices. Moreover, disposable devices eliminate the risk of transmission of diseases between patients. Consequently designers and manufacturers of inflation syringes have worked to limit the expense of such disposable inflation syringes to make them more cost-effective for a wide variety of applications. As a result, there has been an emphasis in favoring more simple designs over more complex apparatus. Such designs typically comprise a simple digital or analog readout of the inflation pressure on the display provided in connection with the inflation syringes.

One typical display of electronically monitored syringes comprises a 7-segment LED display having three to five fields, and perhaps a decimal point. Such simplistic displays are limited in the information they can convey. Some displays provide only the current pressurization of the syringe. Higher-end models may allow the user to toggle the display to view additional information. Although the ability to view additional information can be useful, the user is required to expend mental effort and time to access the additional information, interpret the relevance of the data, and determine how the different values interrelate. Still more expensive syringes may have multiple 7-segment LED displays so as to display multiple values simultaneously. Yet, even with multiple values displayed, a user expends time and mental effort to interpret and relate the values, and to remember which displays represent given values.

BRIEF SUMMARY OF THE INVENTION

The present invention relates to an inflation syringe having an improved display and modularized component assembly. More particularly, the present invention relates to methods and apparatus for providing both numeric and non-numeric indications of an inflation pressurization associated with the inflation syringe. According to one embodiment of the present invention, a progressive non-numeric display is provided for displaying the pressurization of the inflation syringe along with numeric indicators of the pressurization.

According to one aspect of the present invention, the progressive display includes a plurality of indicia corresponding to a range of inflation pressurization values. The indicia are actuated to exhibit a given pressurization in a clear and intuitive manner that allows the practitioner to: (1) easily monitor the general intensity of the pressurization; (2) intuitively track changes in the pressurization; and (3) simply observe the relationship of multiple pressurization values without needing to rely solely on more time consuming and less intuitive interpretation of numeric displays. This permits the user to ascertain the relationship between the current pressurization, desired pressurization amounts, and the rate of pressurization in a straightforward and helpful manner.

According to one aspect of the present invention, the display includes a numeric display for representing the pressurization as a numeric value in addition to the non-numeric display. This provides an additional indication of the inflation pressurization that complements the visual indication provided by the non-numeric display. By providing the numeric display and the associated numeric value of the pressurization, a user can identify more minute incremental changes to pressurization and can easily ascertain the precise numeric value of a given pressurization.

The present invention also relates to a method of displaying non-numeric indicia representing inflation pressurization. In the method, a plurality of indicia are provided to signal changes in the inflation pressurization. Once an initial pressurization is indicated, the current pressurization and changes in pressurization can be displayed to the user in a simple and intuitive manner. For example, one or more of the indicia can be actuated as an indication of the current pressurization. In response to a change in the pressurization, a different one of the indicia is actuated to represent the change in pressurization.

According to another aspect of the present invention, the user interface provides one or more desired types of additional data such as a last maximum pressurization value, a maximum routine pressurization value, or other pressurization values that are different from the current pressurization. For example, one or more of the indicia are identified as an indicator of a representative pressurization such as a maximum pressurization experienced during the current inflation routine. The representative pressurization can be indicated to the user at the same time the current pressurization is indicated to the user, such as by illuminating a non-numeric indicia corresponding to such representative pressurization and/or providing a blinking numeric indication of such representative pressurization, or based on the relative positions of the values to one another. For example, during an inflation routine the routine maximum inflation value can be depicted as a single indicia which is at a higher pressurization value than the current pressurization which may be at a lower pressurization. In response to a change in the pressurization, a different one of the indicia is actuated to represent the change in pressurization while the routine maximum inflation value can remain unchanged. In one embodiment, the non-numeric indicia of current and representative pressurization values can be shown together allowing the user to simply and intuitively determine the relationship between the two values. According to another embodiment, the representative pressurization value may be illuminated by a flashing, blinking or different illumination intensity to distinguish the representative pressurization value as compared to the current pressurization value.

These and other objects and features of the present disclosure will become more fully apparent from the following description and appended claims, or may be learned by the practice of the invention as set forth hereinafter.

BRIEF DESCRIPTION OF THE DRAWINGS

In order to describe the manner in which the above recited and other advantages and features of the invention may be obtained, a more particular description of the invention briefly described above will be rendered by reference to specific embodiments thereof, which are illustrated in accompanying drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION

The present invention relates to an inflation syringe having an improved display and modularized component assembly. More particularly, the present invention relates to methods and apparatus for providing both numeric and non-numeric indications of inflation pressurization associated with the inflation syringe. According to one embodiment, a progressive non-numeric display is provided for displaying the pressurization of the inflation syringe along with numeric indicators of the pressurization. The progressive display includes a plurality of indicia corresponding to a range of inflation pressurization values. The indicia are actuated to display a given pressurization and to allow the practitioner to not only easily monitor the general intensity of the pressurization but also to monitor changes in the pressurization without needing to interpret numerical values. This permits the user to quickly ascertain the relationship between the current pressurization, the desired pressurization, and the rate of pressurization.

According to one aspect of the present disclosure, the progressive display includes a numeric display for representing the pressurization as a numeric value. This provides an additional, precise indication of the inflation pressurization that complements the visual indication provided by the non-numeric indicia. According to another aspect of the present invention, a user interface is provided allowing the user to input information that can be used to automatically identify a target pressurization or a routine maximum pressurization value. The user interface may also allow the user to select other parameters to be displayed.

A method of displaying a pressurization is also provided according to one aspect of the present invention. In the method, a plurality of indicia adapted to signal changes in the inflation pressurization are provided. One or more of the indicia are identified as an indicator of a desired pressurization such as a routine maximum pressurization. Once a desired pressurization is selected, the inflation pressurization is monitored. One or more of the indicia are actuated as an indication of the pressurization. In response to a change in the pressurization, a different one of the indicia is actuated.

Figure 1:
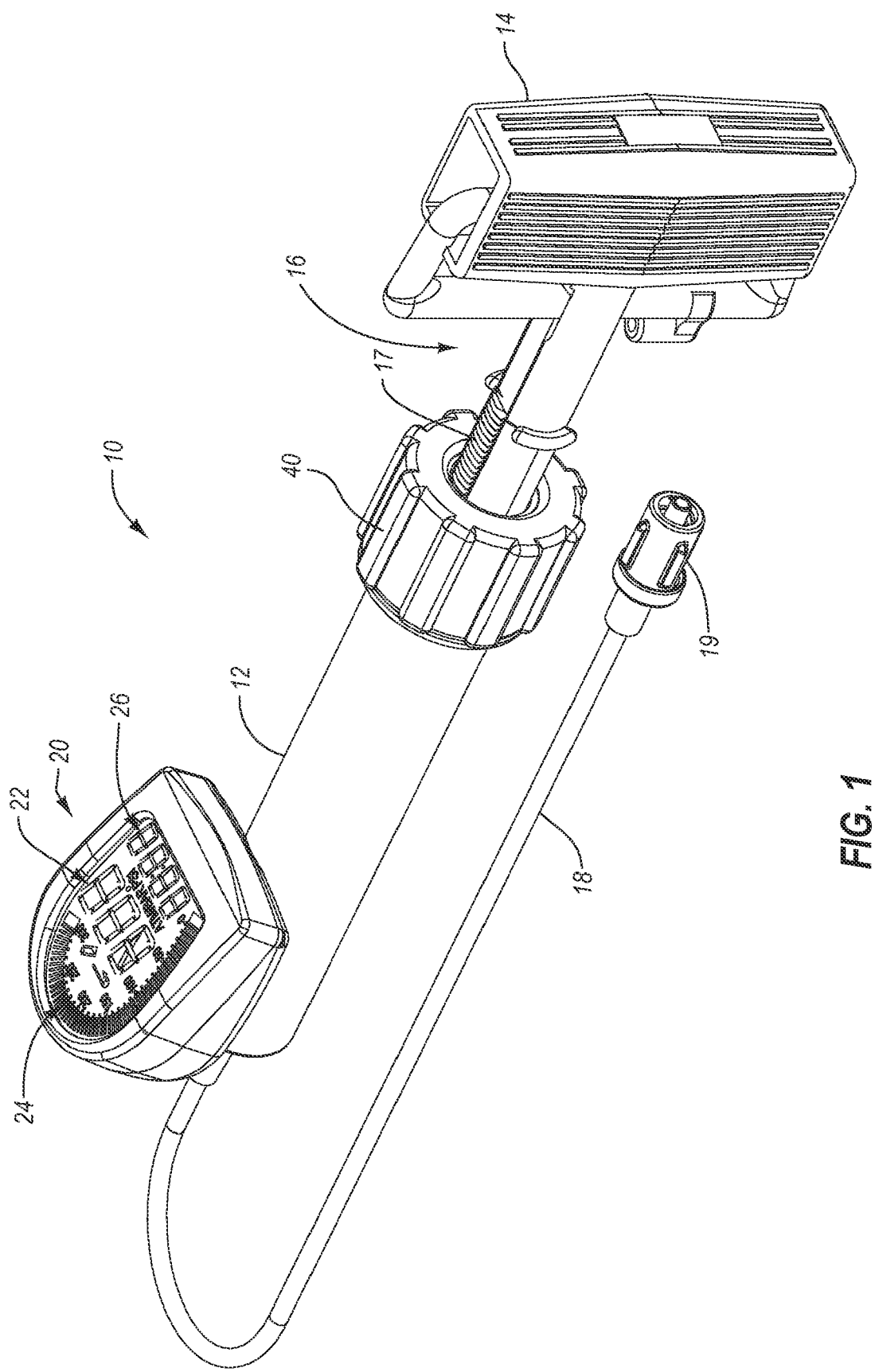
FIG. 1 is a perspective view of an inflation syringe having a display which provides both numeric and non-numeric indicia to represent the pressurization of the inflation syringe.

FIG. 1 illustrates an inflation syringe 10 according to one embodiment of the present invention. Inflation syringe 10 comprises a barrel 12, a plunger 16 and a display 20. Barrel 12 includes an inner lumen which is adapted to hold a pressure transducing medium such as saline or another fluid. Plunger 16 is adapted to increase or decrease the pressurization within barrel 12. Display 20 displays the pressurization information to the user in a simple and intuitive manner.

In the illustrated embodiment, barrel 12 is substantially tubular in configuration. A syringe plunger 16 is configured to be slidably mounted within barrel 12. Plunger 16 includes a threaded portion 17 which is configured to mate with corresponding threads of a plunger retaining nut 40. Plunger retaining nut 40 secures plunger 16 within barrel 12. Tubing 18 is coupled to barrel 12 at one end, and to a rotatable luer coupler 19 at an opposite end. Rotatable luer coupler 19 is adapted to connect tubing 18 to a balloon catheter (not depicted) or another inflatable medical device.

The proximal end of plunger 16 is positioned within the interior of barrel 12 in a fluid-tight manner such that advancing plunger 16 into barrel 12 creates positive pressure within barrel 12. The distal end of plunger 16 comprises a handle 14 which enables a user to apply pressure to push plunger 16 further into barrel 12 or to withdraw plunger 16 from barrel 12. The positive pressure exerted on the fluid contained within barrel 12 is applied to a balloon catheter through tubing 18. Tubing 18 is connected to the balloon catheter by means of a rotatable luer coupler 19. Similarly, by withdrawing plunger 16 toward the rear of the barrel 12, the positive pressure exerted on the balloon catheter may be decreased. According to one embodiment of the present invention, the process of pressurizing barrel 12 to a desired pressurization and then depressurizing barrel 12 to a zero or slightly negative pressurization can be considered an inflation routine.

In the illustrated embodiment, a display 20 is mounted to the exterior of barrel 12. Display 20 provides an intuitive and easy to read configuration. In the illustrated embodiment, display 20 includes a numeric display 22, non-numeric display 24, and a timer display module 26. By providing both a numeric display 22 and non-numeric display 24, display 20 allows a user to read and understand a wider variety of information than provided by existing displays. Additionally, display 20 provides pressurization information in a helpful and intuitive manner eliminating the time and mental effort required for a user to interpret the output of existing displays. In this manner, a practitioner can focus on other aspects of the procedure to be performed without needing to focus on interpreting individual numeric or other information provided by existing displays.

In the illustrated embodiment, display 20 is coupled to a pressure sensing apparatus such as a pressure transducer. The pressure sensing apparatus may be integrated within the wall of barrel 12, mounted within barrel 12, positioned in fluid communication with the interior of barrel 12, or otherwise configured to detect the pressure inside barrel 12. As used to describe the relationship of the pressure sensing apparatus and the interior of barrel 12, the term "fluid communication" may include pneumatic or hydraulic transmission (direct or indirect) of fluid pressures exerted within barrel 12 and tubing 18 to the pressure sensing apparatus so that such fluid pressures can be sensed by the pressure sensing apparatus. Direct transmission of such fluid pressures can be provided, for example, by means of a diaphragm of a piezoresistive semiconductor transducer which is placed into contact (either pneumatically or hydraulically, or a combination of both) with a fluid contained in a closed system. Indirect transmission can occur, for example, where the transducer means is coupled to a diaphragm that in turn contacts the fluid contained in a closed system.

The pressure sensing apparatus may be coupled to display 20 on the exterior of barrel 12 so as to communicate pressurization information associated with the interior of barrel 12. In another embodiment, the pressure sensing apparatus may be integrated with display 20 and in fluid communication with the interior of barrel 12, so as to detect pressurization within barrel 12. In one embodiment, a pressure sensing apparatus is located at the end of connecting tubing attached through a T-connector to tubing 18. Alternatively, the pressure sensing apparatus can be mounted as part of the electronic circuitry contained inside of display 20. In yet another embodiment, the pressure sensing apparatus is located at another position remote from the barrel 12. The pressure sensing apparatus can comprise a piezoresistive semiconductor type transducer. In still another embodiment the pressure sensing apparatus may comprise transducer apparatus other than a piezoresistive or semiconductor apparatus. For example, in one embodiment the pressure sensing apparatus comprises a conventional strain gauge transducer, which has been known and used in the art for many kinds of different pressure monitoring applications, or fiberoptic transducers.

As will be appreciated by those skilled in the art, a variety of types and definitions of inflation routines can be utilized without limiting the scope of the invention. By way of example, and not by limitation, an inflation routine may begin when pressurization of barrel 12 begins, and can include several instances of advancing plunger 16 within barrel 12 and retracting plunger 16 from barrel 12. The inflation routine may end when all pressure is released from barrel 12 such that the pressurization within the barrel falls below a predetermined threshold such as zero pounds per square inch (psi), or a slightly negative pressurization such as −3 psi. In another exemplary embodiment, an inflation routine may begin when positive pressurization is exerted within barrel 12 and ends at the conclusion of a first period of depressurization of the barrel. In one embodiment, not all of the pressurization may be released from barrel 12 at the end of the first period of depressurization. Thus, if not all pressure is released from barrel 12, the next inflation routine may begin when an increase in pressurization is again detected, even where the pressurization is at a lower value than the maximum pressurization value of the previous inflation routine. Additionally, an inflation routine may be utilized with a pressurization mechanism other than an inflation syringe.

As will be appreciated by those skilled in the art, the function of inflation syringe 10 can be provided by a variety of syringe or pressurization systems, without departing from the scope and spirit of the present invention. In one embodiment, a pump device that is pressurized by a plunger or similarly functioning component that is actuated multiple times, and that releases the pressure through a valve is utilized instead of a barrel and plunger syringe system. In another embodiment an automatic pressurization device may provide the required pressure to tubing and the pressure in the tubing may be detected and monitored. A more complete description of one embodiment of a syringe system is contained in U.S. Pat. No. 5,057,078.

Figure 2:
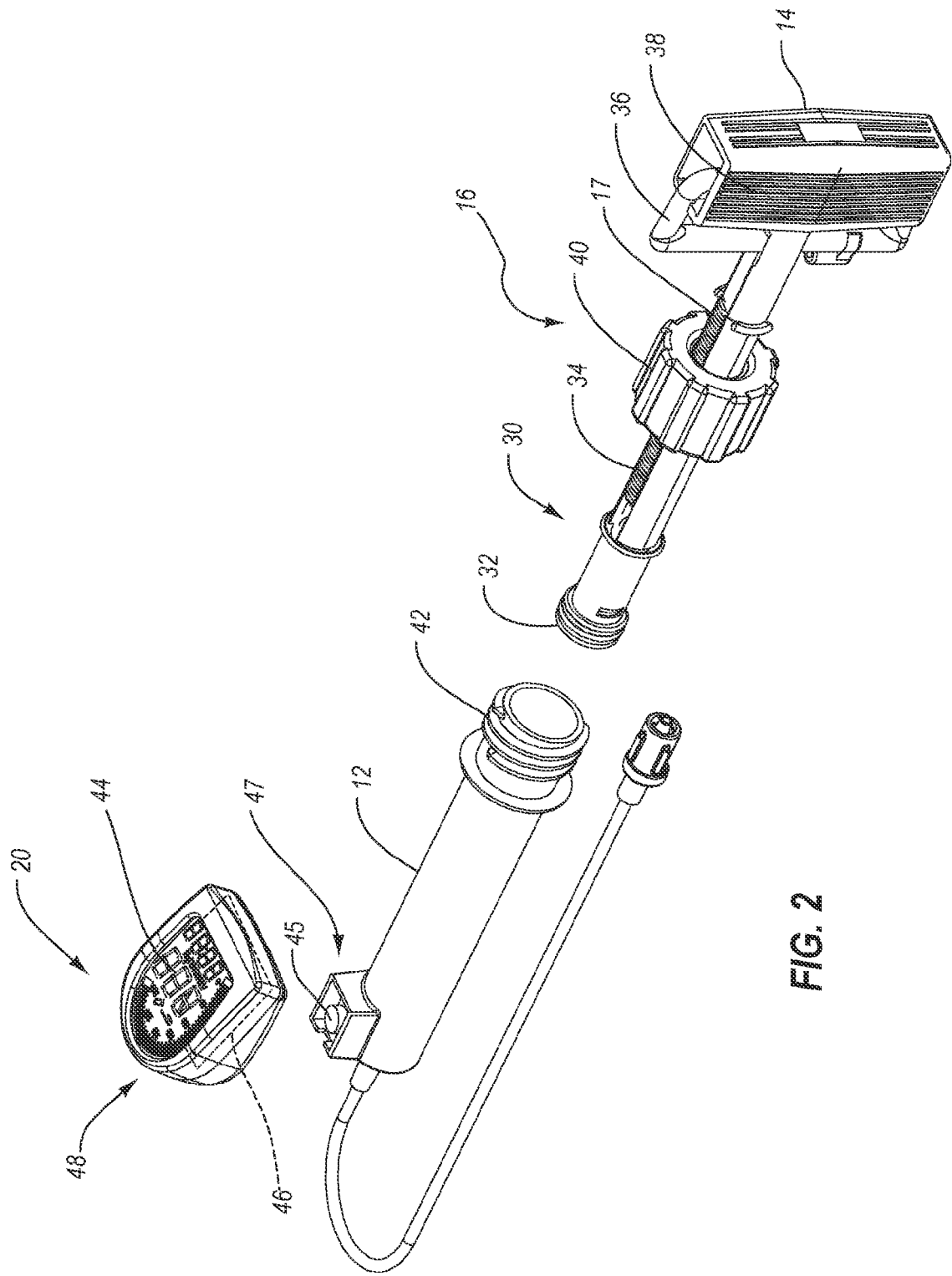
FIG. 2 is an exploded view of the inflation syringe of FIG. 1 illustrating the components of the inflation syringe.

FIG. 2 is an exploded view of inflation syringe 10 of FIG. 1, illustrating the components of inflation syringe 10. In the illustrated embodiment, plunger 16 and handle 14 are shown separately from barrel 12. Plunger 16 comprises a proximal end 30, a rubber tip 32 and threads 34. The distal end of plunger 16 includes a handle receiving component 38 and a spring-activated trigger 36.

In the illustrated embodiment, rubber tip 32 is positioned at proximal end 30 of plunger 16. Rubber tip 32 is adapted to engage the interior of barrel 12 in a fluid-tight manner to allow the user to increase the pressurization on fluid positioned within barrel 12. As the user advances plunger 16 further into barrel 12, rubber tip 32 is also advanced to increase the positive pressure within barrel 12. Similarly, the user can retract plunger 16 in a rearward direction within barrel 12 to decrease the pressurization within barrel 12.

In the illustrated embodiment, plunger 16 is secured within barrel 12 by plunger retaining nut 40. The configuration of retaining nut 40 allows a user to secure plunger 16 within barrel 12 by threadably coupling retaining nut 40 to barrel securement threads 42. The configuration of retaining nut 40 secures plunger 16 within barrel 12 while allowing for slidable movement of plunger 16 in forward and rearward directions within barrel 12. In the illustrated embodiment, barrel securement threads 42 are adapted to cooperatively engage one or more additional components of inflation syringe 10. For example, barrel securement threads 42 can be adapted to mate with a second set of corresponding threads integrated within plunger retaining nut 40.

The distal end of plunger 16 includes a handle receiving component 38 which is configured to accept and engage a spring-activated trigger 36. In the illustrated embodiment, a user can advance syringe plunger 16 without engagement of threads 17 by actuating spring-activated trigger 36. When the user actuates spring-activated trigger 36, a portion of trigger 36 is retracted into handle receiving component 38. Retracting spring activated trigger 36 into handle receiving component 38 disengages threads 34 from the corresponding threads of plunger retaining nut 40. As a result, plunger 16 can freely slide in either a proximal direction or distal direction within barrel 12. By releasing the compression on trigger 36 relative to handle receiving component 38, threads 34 are then permitted to engage the corresponding threads of plunger retaining nut 40. Engagement between threads 34 and plunger retaining nut 40 allows plunger 24 to be advanced or retracted by screwing plunger 16 either in a clockwise or counter clockwise direction respectively.

Trigger 36 allows the user to rapidly provide an increase or decrease of pressurization within barrel 12 of inflation syringe 10. In other words, a user can compress trigger 36 against handle receiving component 38 and threadlessly advance or retract plunger 16 within barrel 12 to increase or decrease the pressurization within barrel 12. The user can then release trigger 36 and threadably advance or retract plunger 16 within barrel 12 to provide a more gradual adjustment of plunger 16 to a more exacting desired pressurization. Additionally, threadably advancing plunger 16 within barrel 12 can be utilized to provide greater pressurization within barrel 12 than can be accomplished by threadless advancement alone.

In the illustrated embodiment, the body of syringe barrel 12 includes a mounting bracket 110. Mounting bracket 110 provides a mechanism for securing display 20 to syringe barrel 12. Mounting bracket 110 is integrally coupled to the proximal, or leading end, of barrel 12. In the illustrated embodiment, mounting bracket 110 is in fluid communication with the interior of barrel 12 through an opening (not depicted) formed in the sidewall of barrel 12 for the purpose of communicating pressurization information from the interior of barrel 12.

In the illustrated embodiment a display 20 is provided to relate pressurization information to a user. Display 20 includes a display module 44 and a housing 48. Housing 48 is adapted to receive display circuitry 46 and display module 44. Housing 48 is adapted to secure display module 44 such that it is viewable to a user.

In the illustrated embodiment, display module 44 may comprise a numeric indicia, non-numeric indicia, and/or a timer display module. By providing numeric and non-numeric indicia, a simple and intuitive display of pressurization information can be provided to a user. Display module 44 is an example of a means for displaying inflation pressurization information. Display circuitry 46 processes electrical signals representing pressurization information that are output by a pressure sensing apparatus 45. Display circuitry 46 can also control the manner in which the display module 44 displays the pressurization information. The display circuitry is discussed as an example of a means for processing electrical signals from a sensor apparatus. Other examples of a means for processing electrical signals can include, but are not limited to, a microchip, a personal computer, and a handheld device such as a personal digital assistant (PDA). A method of displaying pressurization information using numeric indicia and non-numeric indicia is discussed below in conjunction with the discussion of FIGS. 4 and 5.

According to one aspect of the present invention, a pressure sensing apparatus 45 is provided. Pressure sensing apparatus 45 is positioned in fluid communication with the interior of barrel 12. In the illustrated embodiment, pressure sensing apparatus 45 is operably connected to the display circuitry when display 20 is secured relative to barrel 12. In the illustrated embodiment, display 20 is secured to barrel 12 utilizing mounting bracket 47.

As will be appreciated by those skilled in the art, a variety of types and configurations of displays can be utilized without departing from the scope and spirit of the present invention. According to one embodiment of the present invention, the display is provided separately from the inflation syringe. For example, the display can be provided as part of a reusable user interface which is operably connected to a disposable inflation syringe. In one embodiment, the display comprises a negative polarity or reverse polarity LED display. In another embodiment, the display comprises a LED/LCD combination display. Other examples of means for displaying inflation pressurization can also be utilized including, but not limited to, a cathode ray tube display, a liquid crystal display (LCD) screen, a grouping of light emitting diodes (LEDs), a handheld device such as a personal digital assistance (PDA), and a printer for printing out a hard copy display.

Figure 3A:
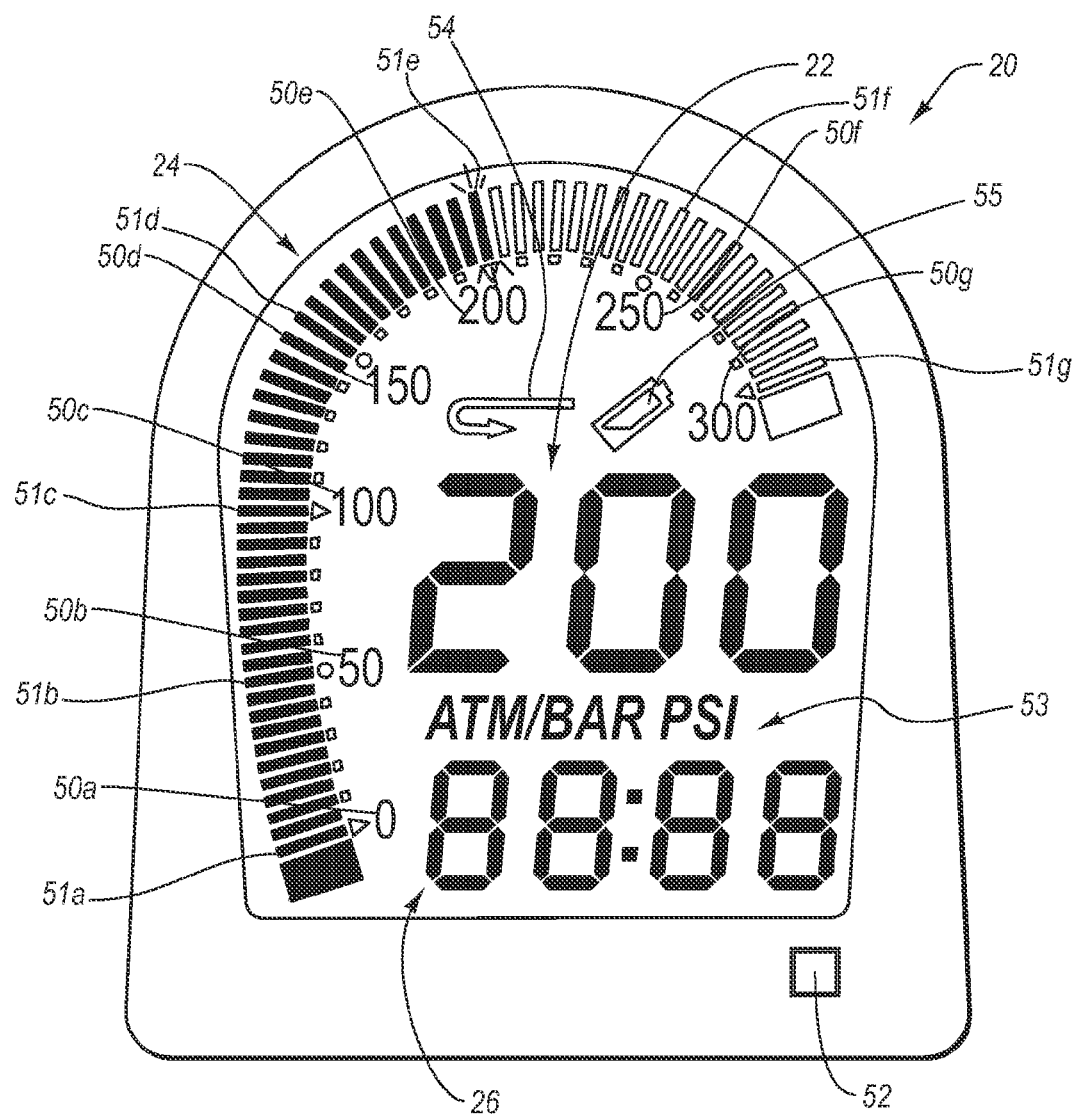
FIG. 3A illustrates a display of an inflation syringe comprising numeric and non-numeric indicia displaying the current pressurization of the inflation syringe

FIGS. 3A through 3D depict a display 20 having numeric and non-numeric indicia for displaying pressurization information to a user in a simple and intuitive manner according to one aspect of the present invention. With reference now to FIG. 3A, in the illustrated embodiment, display 20 includes a non-numeric display 24 and numeric display 22. Non-numeric display 24 comprises a plurality of indicia 51. Indicia 51 are configured to provide a progressive display which depicts the pressurization of the inflation syringe in a simple and intuitive manner. The progressive configuration of display 24 and corresponding indicia 51 can provide an indication of a range of inflation pressurization values. As indicia 51 are actuated, the user can quickly and simply determine the pressurization of the inflation syringe 10 allowing the practitioner to not only easily monitor the general intensity of the pressurization but also to monitor changes in the pressurization without needing to interpret numerical values. As a result, the user can quickly ascertain the relationship between the current pressurization, the desired pressurization, and the rate of pressurization without needing to interpret numeric values. In the illustrated embodiment, alternative measurements values other than pounds per square inch (psi), such as atmospheres or bar are provided.

In the illustrated embodiment, numeric display 22 of display 20 provides a numeric indication of the pressurization in the inflation syringe. Numeric display 22 provides an additional, precise indication of the inflation pressurization that complements the visual indication provided by the non-numeric indicia 51. In the illustrated embodiment, numeric display 22 comprises a digital display, such as a 7-segement LED display having multiple fields. As depicted, numeric display 22 includes three fields, each field representing a digit of the numeric value. Numeric display 22 displays a current pressurization value.

In the illustrated embodiment, display 20 further comprises a timer display module 26. Timer display module 26 is adapted to provide an indication of the length of an inflation routine, the length of time between inflation routines, the length of time at a particular pressurization value, and/or the length of time that inflation pressure is applied to an attached inflatable medical device. Display 20 may also include a maximum value actuation button 52. Maximum value actuation button 52 allows a user to toggle the numeric display 22 to display the maximum pressurization value achieved during the current, most recent, or other selected, inflation routine.

In the illustrated embodiment, an exemplary current pressurization value of the inflation syringe is displayed as 200 pounds per square inch (psi). The numeric display 22 is configured to provide a precise, intuitive indication of a value, which typically is the current pressurization of the interior of barrel 12 (see FIG. 1). During an inflation routine, numeric display 22 is automatically updated in real-time to provide the practitioner with an immediate, intuitive indication of the pressurization within the interior of the barrel and/or the tubing of the inflation syringe. The depicted 7-segment LED display is provided as an exemplary display capable of providing a straightforward and easy-to-read, digital display.

As previously discussed, in the illustrated embodiment non-numeric display 24 includes a plurality of non-numeric indicia 51. In the illustrated embodiment, non-numeric indicia 51 and display 20 comprises a reverse polarity LED in which a backlit LED is provided in connection with LCD apparatus. Thus illumination is provided by means of the backlit LED and the LCD apparatus controls illumination or the lack of illumination for each component of the display including non-numeric display 24. By utilizing a reverse polarity LED, efficient use of battery power is facilitated allowing for desired longevity of use while minimizing the size and bulk of batteries required. In an alternative embodiment, each of non-numeric indicia 51 comprises a white or colored LED. Additionally, each of the plurality of non-numeric indicia 51 of the non-numeric display 24 can represent one or more pressurization values. A plurality of numeric value indicators 50 are provided in connection with indicia 51 to provide a representation of the pressurization values corresponding to one, or a group of, non-numeric indicia 51.

In the illustrated embodiment, each indicia 51 represents a range of pressurization values corresponding to approximately five psi. The numeric value indicators 50a, b, c, d, e, f, g are spaced along the indicia 51, as shown, with a numeric value indicator corresponding with every tenth indicia 51. As a result, the numeric value indicator 50a which is labeled as "0" clearly illustrates to the user than when no indicia is illuminated, or when indicia 51a alone is illuminated, the pressurization within the inflation syringe is zero psi. An exemplary non-numeric indicia 51b is also depicted. In the illustrated embodiment, indicia 51b is positioned approximately ten non-numeric indicia from indicia 51a. A numeric value indicator 50b which is labeled "50" is provided in connection with indicia 51b representing a pressurization within the inflation syringe of 50 psi. As a result, when the indicia from 50a to 50b are illuminated, the user can quickly and simply determine that the pressurization within the inflation syringe is 50 psi.

As will be appreciated by those skilled in the art, when the pressurization within the inflation syringe is between zero psi and fifty psi, one of the non-numeric indicia 51 positioned between indicia 51a and 51b will be illuminated as the non-numeric representation of the pressurization within the inflation syringe. For example, in the event that the pressurization within the inflation syringe is 35 psi, approximately 7 non-numeric indicia will be illuminated due to the fact that each non-numeric indicia represents a range of five psi of pressurization. In the event that the pressurization within the inflation syringe is 45 psi, approximately 9 non-numeric indicia will be illuminated. The user can quickly ascertain the approximate pressurization within the inflation syringe by how close the last illuminated indicia is to a particular numeric value indicator. For example, when the pressurization in the inflation syringe is 35 psi, the user can quickly identify that the last illuminated non-numeric indicia is greater than zero psi, less than 50 psi. Additionally, the user can quickly identify that the last illuminated non-numeric indicia is closer to 50 psi than 0 psi. As a result, the non-numeric display 24 allows a user to quickly determine the approximate pressurization within the inflation syringe.

In the illustrated embodiment, numeric value indicator 50c indicates that an indicia 51c corresponds with a pressurization value of 100 psi. Numeric indicators 50d through 50g are similarly spaced, and respectively indicate that indicia 51d, 51e, 51f and 51g represent pressurization values 150 psi, 200 psi, 250 psi, and 300 psi, respectively. In the illustrated embodiment, non-numeric indicia 51 are lit in a progressive manner. Thus, all non-numeric indicia 51 representing values less than the current pressurization value remain lit as the pressurization increases and additional non-numeric indicia 51 are illuminated.

In the illustrated embodiment, each of numeric value indicators 50a, b, c, d, e, f, g can toggle between a first state in which an indication of a first measurement variable and a second state in which an indication of a second measurement variable is provided. For example, in FIG. 3B numeric value indicator 50b indicates that indicia 51b corresponds with pressurization value of 50 psi. Additionally, a measurement unit indicator 53 provides an indication that pressurization values are provided in pounds per square inch. In FIG. 3C, measurement unit indicator 53 provides an indication that pressurization values are provided in atmospheres (ATM) or bar (BAR). Additionally numeric value indicator 50b indicates that indicia 51b corresponds with a pressurization value of 3.5 ATM/BAR. As a result, as a user toggles between measurement units of psi and bar, numeric value indicators 50a-g also toggle to clearly show the numeric value of the appropriate measurement unit with which each non-numeric indicia is associated.

According to one embodiment of the present invention, a user presses a maximum value actuation button 52 to toggle between measurement units. Maximum value actuation button 52 can also be utilized to toggle display 20 from displaying current pressurization information to displaying representative pressurization information. In one embodiment, a quick push of button 52 toggles display 20 between psi and ATM/BAR while a button push of n seconds toggles display 20 between current pressurization information and representative pressurization. In the illustrated embodiment, a representative pressurization icon 54 and a low batter indicator 54 are also provided. When representative pressurization icon 54 is illuminated, display 20 is displaying representative pressurization information such as a maximum routine pressurization rather than the current pressurization information. In this manner, the user can quickly determine the information that is being depicted by the display. When low battery indicator 54 is illuminated, the user can quickly determine that the battery level is low. This prevents unanticipated loss of battery power and/or loss of display functionality during a pressurization procedure.

Figure 3B:
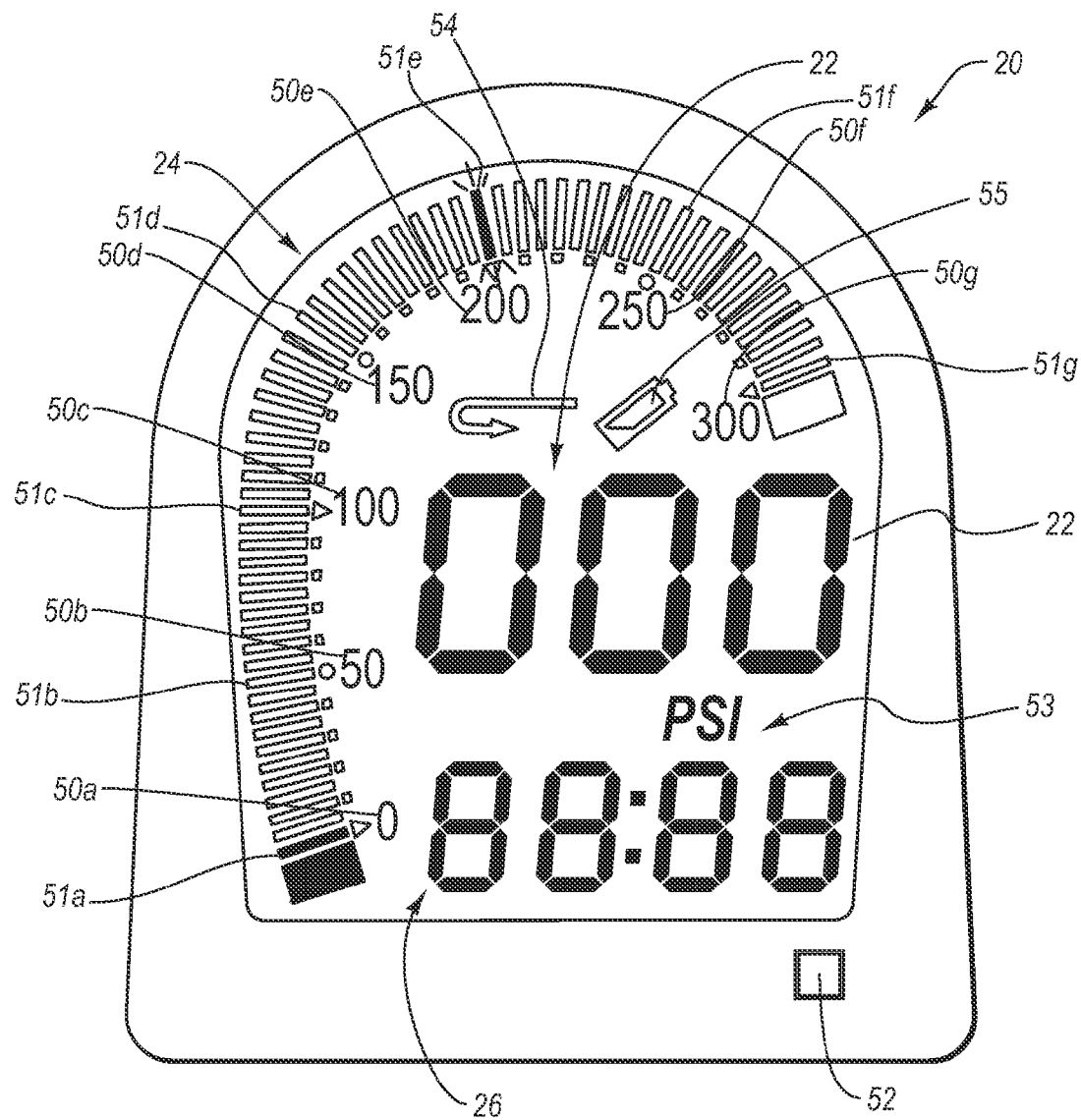
FIG. 3B illustrates the display of the inflation syringe in which representative pressurization value information is displayed to a user utilizing non-numeric indicia.
Figure 3C:
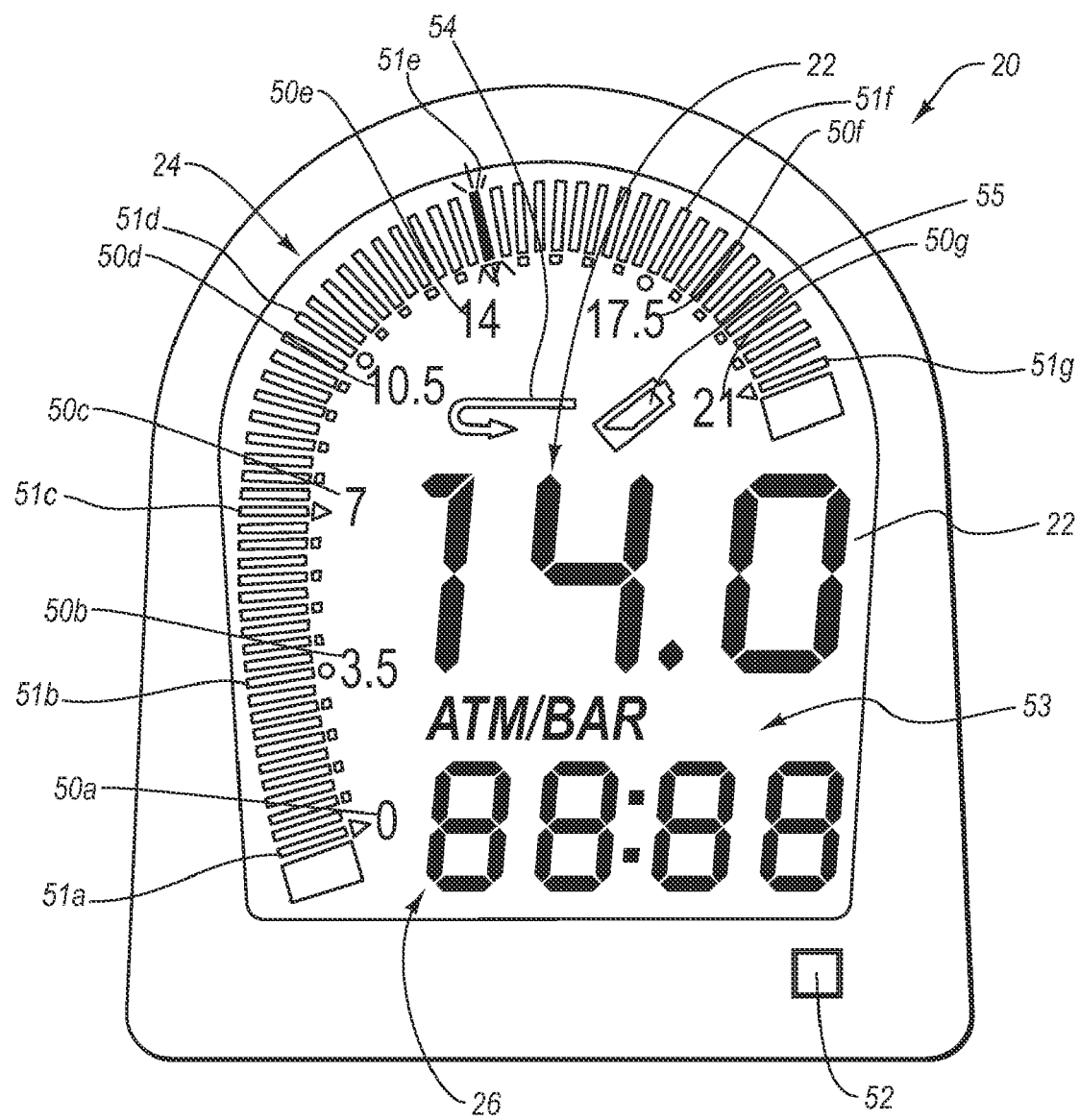
FIG. 3C illustrates the display of the inflation syringe in which representative pressurization value information is displayed to a user utilizing both numeric and non-numeric indicia.

FIG. 3B illustrates a display 20 subsequent to previous pressurization routine of the inflation syringe. In the illustrated embodiment, there is little or no pressurization within the inflation syringe. As a result, numeric display 22 shows a pressurization of zero psi. Additionally, non-numeric indicia 51a-51b are not illuminated.

In the illustrated embodiment, a non-numeric indicia 51e is illuminated. Non-numeric indicia 51 is illuminated as a representation of a value that represents something other than the current pressurization of the inflation syringe. According to one embodiment of the present invention, an indicia 51, such as non-numeric indicia 51e, can be lit to represent a last pressurization value, a routine maximum pressurization value and/or a target pressurization value. To avoid confusion, an indicia 51 representing a last value and/or a target value may appear a different color and/or flash or blink. In the illustrated embodiment, it is fairly simple to ascertain that non-numeric indicia 51 represents a last pressurization value and not the current pressurization value as the indicia between 51a and 51e are not illuminated. As will be appreciated by those skilled in the art, a non-numeric indicia can be illuminated as an indicator of a last pressurization value while current pressurization can also be illuminated.

Display 20 may further comprise a user interface which allows preloading or allowing a user to set a target pressurization value different from the last value. This may be accomplished by adjusting up or down from the displayed last pressurization value, or by manually entering a target value. In still another embodiment, maximum value actuation button 52 can enable the toggling of numeric display 22 between three values, current pressurization, last value, and target value. The target value may also be indicated by the non-numeric display 24, either with the last value or in place of the last value, thus giving a user a visual representation of progress made in pressurizing the barrel, how much progress remains to reach the last value or a desired value, the rate of pressurization, and changes in pressurization resulting from each movement of the plunger within the barrel. Thus, the user can more easily ascertain the force necessary for subsequent movements of the plunger to reach the target pressurization value. The user interface may also enable the user to select other parameters to be displayed.

FIG. 3C depicts display 20 of FIGS. 3A and 3B showing another manner of displaying last value information to a user, immediately after the user has pressed the maximum value actuation button 52. In FIG. 3B, the barrel of the inflation syringe is completely depressurized, as indicated by numeric display 22 and non-numeric display 24. If the user wants to view the exact last pressurization value, this information is not readily represented by indicia 51e because of the multiple possible pressurization values represented by each indicia 51. To view the precise last pressurization value, the user can toggle the display by pressing maximum value actuation button 52. In the illustrated embodiment, the user has pressed the maximum value actuation button 52. Both indicia 51e of non-numeric display 24 and the 7-segment display of numeric display 22 indicate the last value is 200 psi. By displaying the maximum value pressurization information on non-numeric display 24 and numeric display 22, precise pressurization information is provided to a user in intuitive and easy to read manner.

In one embodiment of the present invention, display 20 may automatically toggle to display last value information at the end of an inflation routine. In the embodiment, display 20 will continue to display last value information on both the numeric display 22 and non-numeric display 24 until the beginning of the next inflation routine. At the beginning of the next inflation routine, display 20 may automatically toggle back to display current pressurization value information on numeric display 22 while retaining last value information using non-numeric display 24. According to one embodiment of the present invention the precise maximum value information may be available by pressing maximum value actuation button 52 at any time during the pressurization routine. Indicia 51e may appear a different color and/or flash to indicate it is presently representing a maximum pressurization value. In another embodiment, a user may adjust which indicia is appearing in a different color and/or which indicia is flashing while setting a target value which is different from the last pressurization value.

Figure 3D:
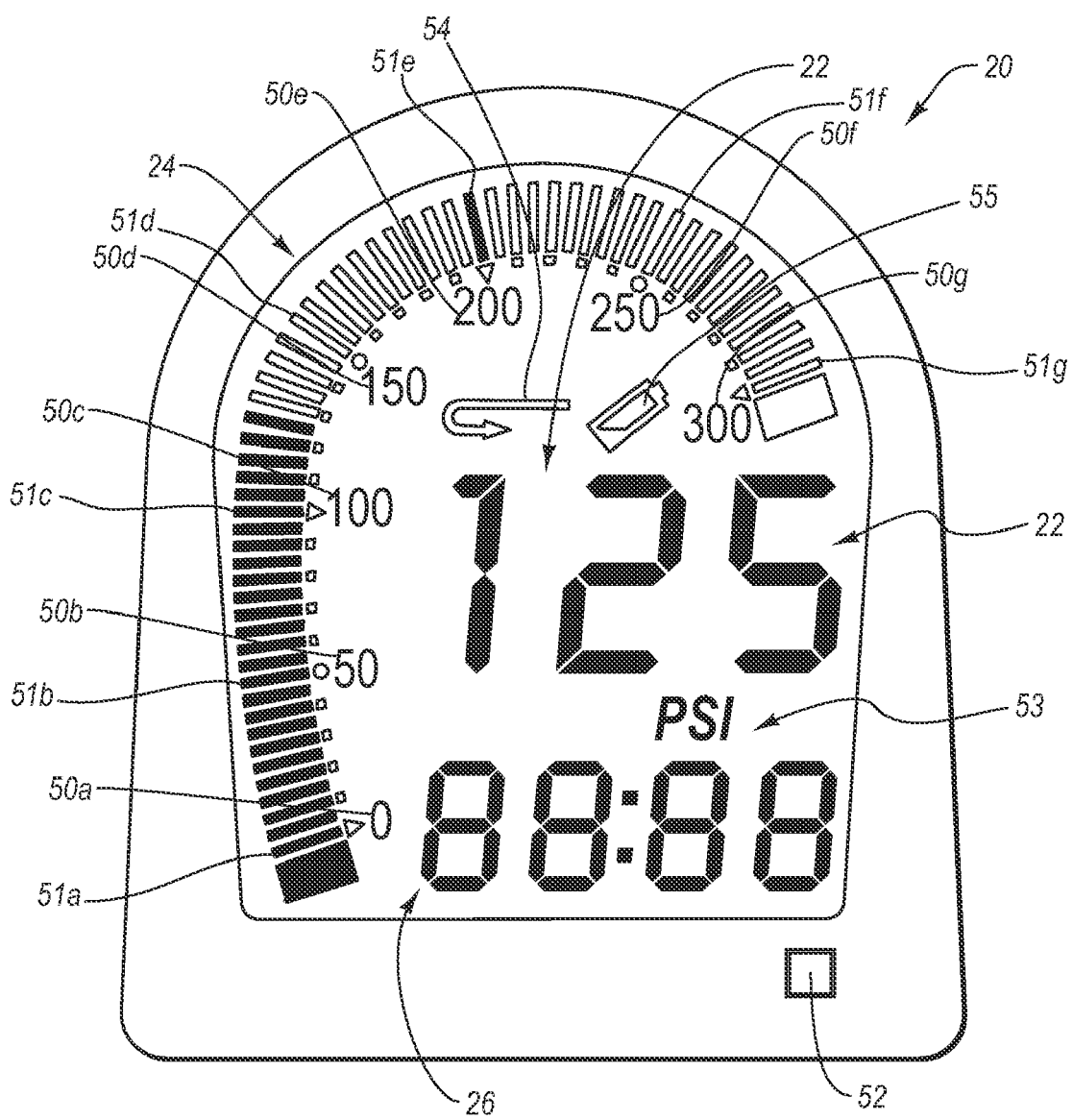
FIG. 3D illustrates the display of the inflation syringe demonstrating operation of the display during pressurization of the inflation syringe.

FIG. 3D illustrates display 20 during a during a period of pressurization during the pressurization routine in which the current pressurization of the inflation syringe is less than the maximum routine pressurization value. In the illustrated embodiment, non-numeric indicia 51e is illuminated as an indicator of the maximum pressurization value. In other words, non-numeric indicia 51e allows a user to quickly determine the maximum routine pressurization of the inflation syringe during the current inflation routine. Because non-numeric indicia 51e corresponds with an exemplary pressurization value of 200 psi, the user can quickly determine that a maximum pressurization of 200 psi was reached during the current pressurization routine. This may be helpful where a practitioner desires to apply a similar, lesser or greater pressurization during the current pressurization routines. The configuration of display 20 allows a user to quickly ascertain the present pressurization value, the progress made and remaining to reach the maximum routine pressurization value and/or another representative pressurization value, the rate of pressurization, and the progress made with each movement of the plunger, in an intuitive and simple to read manner.

In the illustrated embodiment, indicia 51a through 51c are illuminated. Additionally, approximately 5 additional indicia positioned between indicia 51c and 51d are illuminated. Because indicia 51c represents a pressurization of 100 psi, the user can quickly and simply ascertain that the pressurization in the inflation syringe represents a pressurization which is greater than 100 psi. Additionally, due to the fact that indicia 51 corresponds with a pressurization of 150 psi, the user can quickly ascertain that the current pressurization in the inflation syringes represents a pressurization that is less than 150 psi. Due to the progressive nature of non-numeric indicia 51 and non-numeric display 24, the user can visually determine that the pressurization is approximately 125 psi due to the fact that the last illuminated non-numeric indicia 51*d* is positioned approximately midway between 100 psi and 150 psi. This can be quickly confirmed by simply glancing at numeric indicia 22 which confirms that the pressurization in inflation syringe is exactly 125 psi.

Providing a non-numeric display 24 in connection with a numeric display 22 provides an intuitive and simple to read display while also displaying more information simultaneously on the display than can be depicted on a numeric display alone. For example, the numeric display 22 can provide a current pressurization value while the non-numeric display 24 simultaneously displays a current pressurization value and a representative pressurization value. In the illustrated embodiment, the user can determine the approximate pressurization of the inflation syringe utilizing the non-numeric display 24. Additionally, the user can quickly and easily identify the relationship between the current pressurization and a target or last pressurization value. Additionally, the non-numeric display 24 can provide a visual representation of progress previously made in pressurizing the barrel, and of how much additional pressurization in needed to reach a desired value, such as the last pressurization value or a target pressurization value. For example, the user is provided with a visual indication that the current pressurization of 125 psi is approximately two-thirds of the last pressurization value represented by non-numeric indicia 51*e*. Additionally, the user can quickly ascertain that the current pressurization is slightly less than half of a maximum pressurization of 300 psi which corresponds with a non-numeric indicia 51*g*.

Display 20 also allows a user to easily monitor the rate of pressurization and changes in pressurization resulting from each movement of the plunger within the barrel. Thus, the user can more quickly estimate the force necessary for subsequent movements of the plunger to reach a desired pressurization value. In the illustrated embodiment, the arcuate or curved configuration of non-numeric display 24 allows a user to determine progress along a pressurization curve. The configuration of the pressurization curve provides subtle non-numeric indications in addition to actual pressurization values. For example, a first range of non-numeric indicia corresponding with a first portion of non-numeric display 24 such as the bottom portion of the curve, i.e. indicia 51*a*-51*c,* can quickly be identified as below typically desired maximum pressurization values. As the pressurization approaches a second portion of the non-numeric display 24 such as at the arch or apex of the curve, i.e. indicia 51*d*-51*f,* the difference is shape and configuration of the second portion of the curve as compared to the first portion of the curve allows a user to ascertain that the pressurization is within a range of typically desired maximum pressurization values. As the user passes the second portion of the non-numeric display 24 and moves toward a third portion of the non-numeric display 24, such as the final non-numeric indicia, i.e. 51*f*-51*g,* the user can quickly determine that the pressurization exceeds typically desired maximum pressurization values. In this manner, the shape of the non-numeric indicia provides an indication of the desirability of given pressurization values in addition to actual pressurization values.

As will be appreciated by those skilled in the art, a variety of types and configurations of non-numeric displays can be provided without departing from the scope and spirit of the present invention. For example, a non-numeric display can comprise a progressive guage or dial. In one example, the dial may be digital, comprising indicated by lights (e.g. LEDs), changing colors, notches, and/or other indicia. In another embodiment, rather than comprising a digital gauge or dial, non-numeric display may comprise an analog dial, such as an arm configured to pivot in an arc, moving along increments positioned in a curvilinear fashion on a portion of the arc. In still another embodiment, non-numeric display may comprise an analog gauge that displays a representation of current pressurization and progress of pressurization along a range of possible inflation pressures. According to one embodiment of the present invention, the non-numeric display may comprise indicia arranged in a linear or curvilinear array. In still another embodiment there may be a plurality of instances of non-numeric indicia, each instance representing different pressurization values (e.g. current pressurization and last value). In still another embodiment, the non-numeric indicia may be arranged in a non-linear configuration. In the illustrated embodiment, one side of the arcuate curve is longer than the other side of the curve to represent the respective desired ranges of values previously referenced.

According to an alternative embodiment of the present invention, different colors of pressurization can be provided as the pressurization increases along the pressure curve. For example, at low pressurization, the non-numeric indicia are illuminated green. At medium pressurization, the non-numeric indicia are illuminated yellow. At high pressurizations, the non-numeric indicia are illuminated red.

Figure 4:
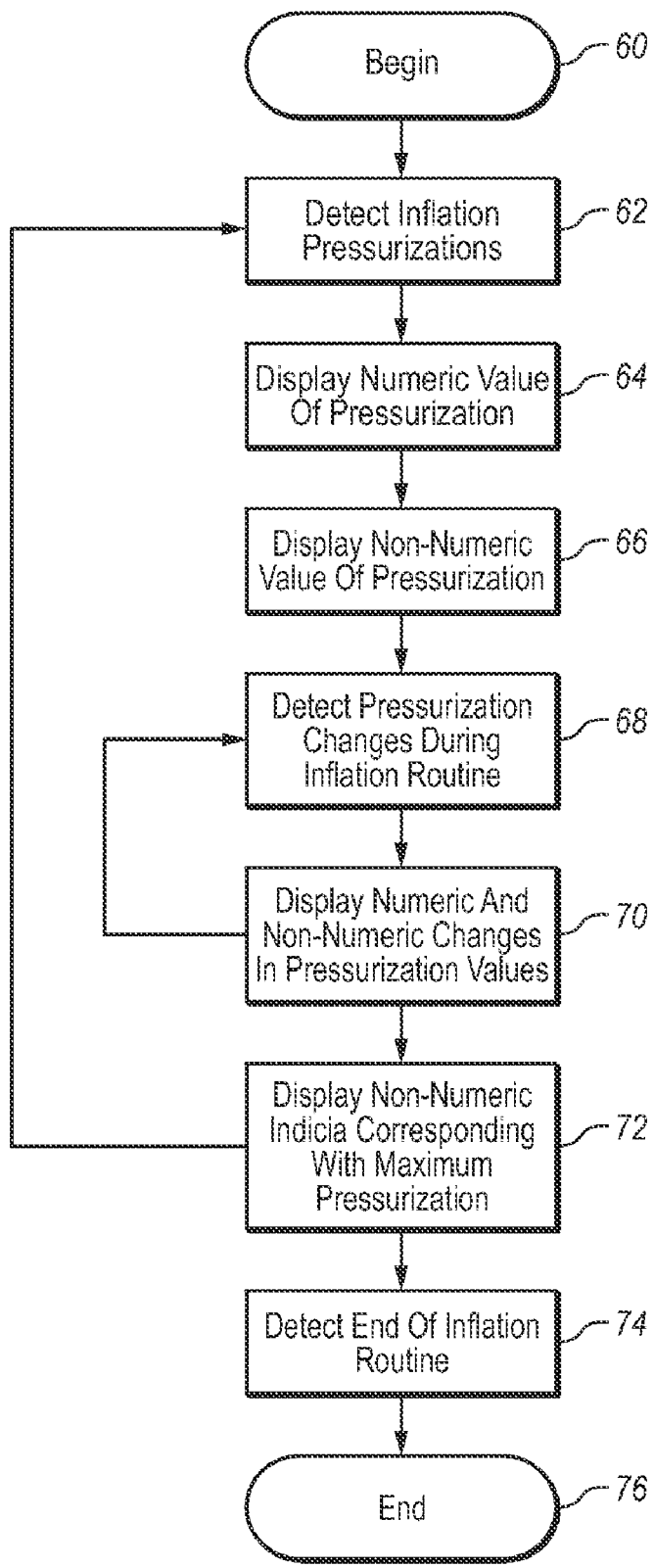
FIG. 4 is a flow chart illustrating of a method of displaying pressurization information utilizing numeric and non-numeric indicia.

FIG. 4 is flow chart depicting a method of displaying pressurization information utilizing numeric and non-numeric indicia, according to one embodiment of the present invention. In the illustrated embodiment, the method begins at a step 60. An inflation pressurization within the interior of the barrel is detected in a step 62. Subsequent to detecting the inflation pressurization, the numeric value of the pressurization is displayed in a step 64. The non-numeric value of the pressurization is then displayed in a step 66. Once the numeric value of the pressurization is displayed in a step 64 and the non-numeric value of the pressurization is displayed in a step 66, a change in pressurization is detected during an inflation routine in a step 68. Once the change in pressurization is detected during the inflation routine, numeric and non-numeric changes in the pressurization values are displayed in a step 70.

Subsequent to detecting of pressurization changes and display of numeric and non-numeric changes in pressurization values during steps 68 and 70, a subsequent change in pressurization may be detected. In the event that a change in pressurization is detected during the inflation routine, step 68 is repeated. Once a change in pressurization is detected and step 68 is repeated, numeric and non-numeric changes in the pressurization values are again displayed in step 70. Non-numeric indicia corresponding to a maximum inflation value is displayed in a step 74. Once the maximum inflation values are displayed, in the event that an inflation pressurization is detected, the method returns to step 62. In the event that an inflation pressurization is not detected, an end of the inflation routine is detected in a step 74. The method ends in a step 76.

The detection of inflation pressurizations may be accomplished by a pressure sensing apparatus, such as a pressure sensing transducer. A display, such as depicted in FIGS. 3A through 3D, may display the numeric value of the pressurization which provides a precise indication of the pressurization value. The display may also display non-numeric indicia as a representation of the value of pressurization. During the inflation routine, the pressure sensing apparatus may detect pressurization changes and then the display may update the numeric indicia and non-numeric indicia to display the changes in pressurization values. Detecting in step 68 and displaying in step 70 changes in pressurization values may occur multiple times during a pressurization routine. The method may also detect the end of the inflation routine and then display non-numeric indicia corresponding to the last value, or the maximum value, of the inflation routine that just ended. According to one embodiment of the present invention, the method may be directed by display circuitry (depicted in FIGS. 1, 2, and 6), and may be implemented in and/or carried out wholly or partially by software and/or hardware components.

Figure 5:
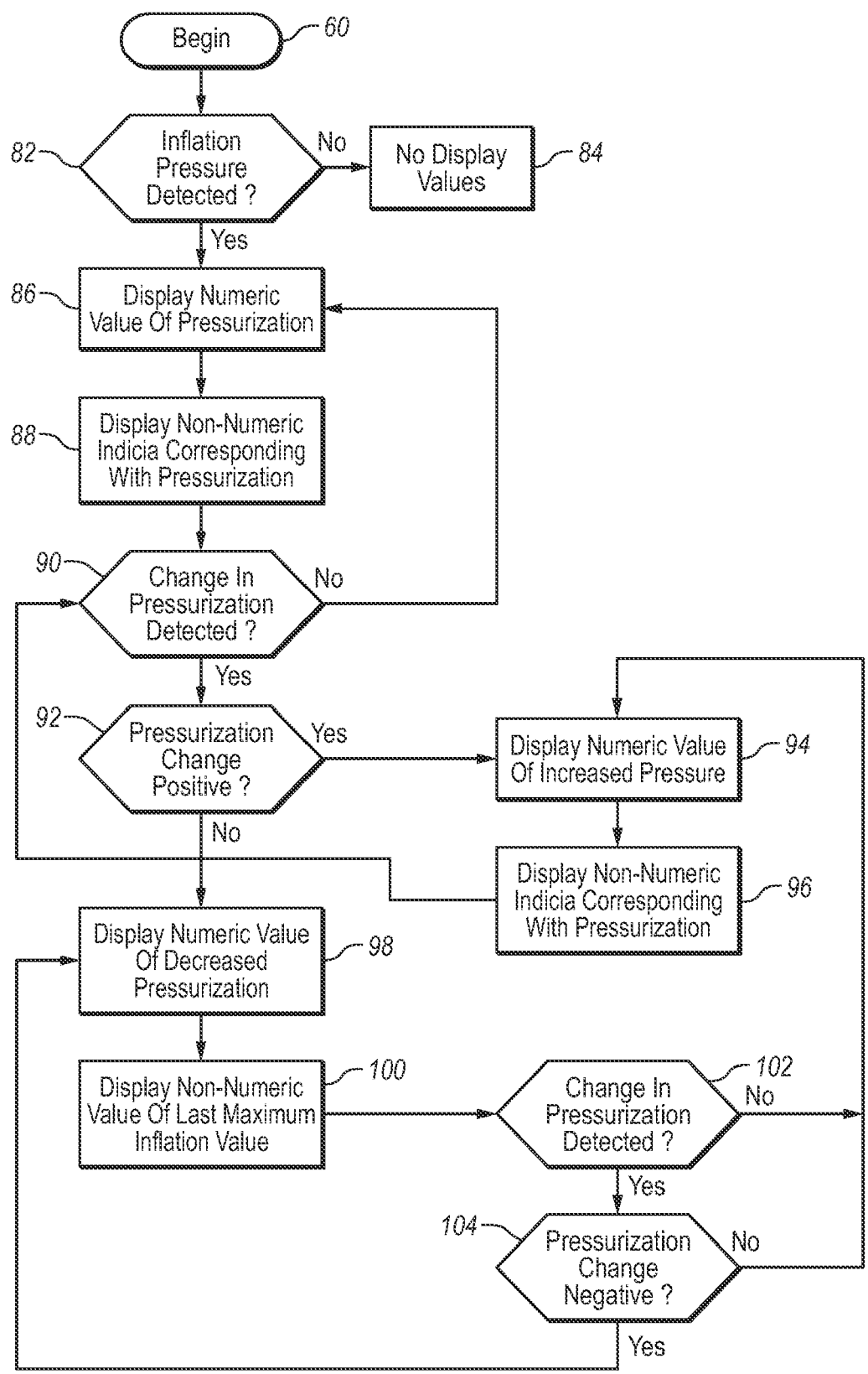
FIG. 5 is a logic flow diagram depicting of a method of displaying pressurization information utilizing numeric and non-numeric indicia.

FIG. 5 depicts a logic flow diagram of another method of displaying pressurization information utilizing numeric and non-numeric indicia, according to one embodiment of the present invention. The method begins at a step 60. A determination is performed of whether an inflation pressurization is detected in a step 82. If no pressurization is detected, no pressurization value is displayed in a step 84. If inflation pressurization is detected, a numeric value of the pressurization is displayed in a step 86. Non-numeric indicia corresponding with the value of pressurization is then displayed in a step 88. The pressure sensing apparatus may continue to detect changes in pressurization in a step 90. If no change is detected, the current pressurization value may continue to be displayed using numeric indicia in a step 86 and non-numeric indicia in a step 88. If a change of pressurization is detected in step 90, it is determined whether the change in pressurization is positive in a step 92.

In the event that the change in pressurization is positive, the numeric value of the increased pressurization is displayed in a step 94. Once the increased pressurization is displayed, non-numeric indicia corresponding with the pressurization is displayed in a step 96. The method again returns to a step 90 in which it is determined whether a change in pressurization is detected.

Returning to step 92, in the event that the change of pressurization is not positive, the numeric value of the decreased pressurization is displayed in a step 98. Once the numeric value of the decreased pressurization is displayed, non-numeric indicia indicative of the last maximum inflation value is displayed in a step 100. It is then determined whether further changes in pressurization are detected in a step 102. If a change in pressurization is detected, it is then determined if the change in pressurization is negative in a step 104. If the change in pressurization is negative, the method returns to step 98 and the numeric value of the decreased pressurization is again displayed. If the change in pressurization is positive, the method returns to step 94 in which the numeric value of the increased pressurization is displayed.

Figure 6:
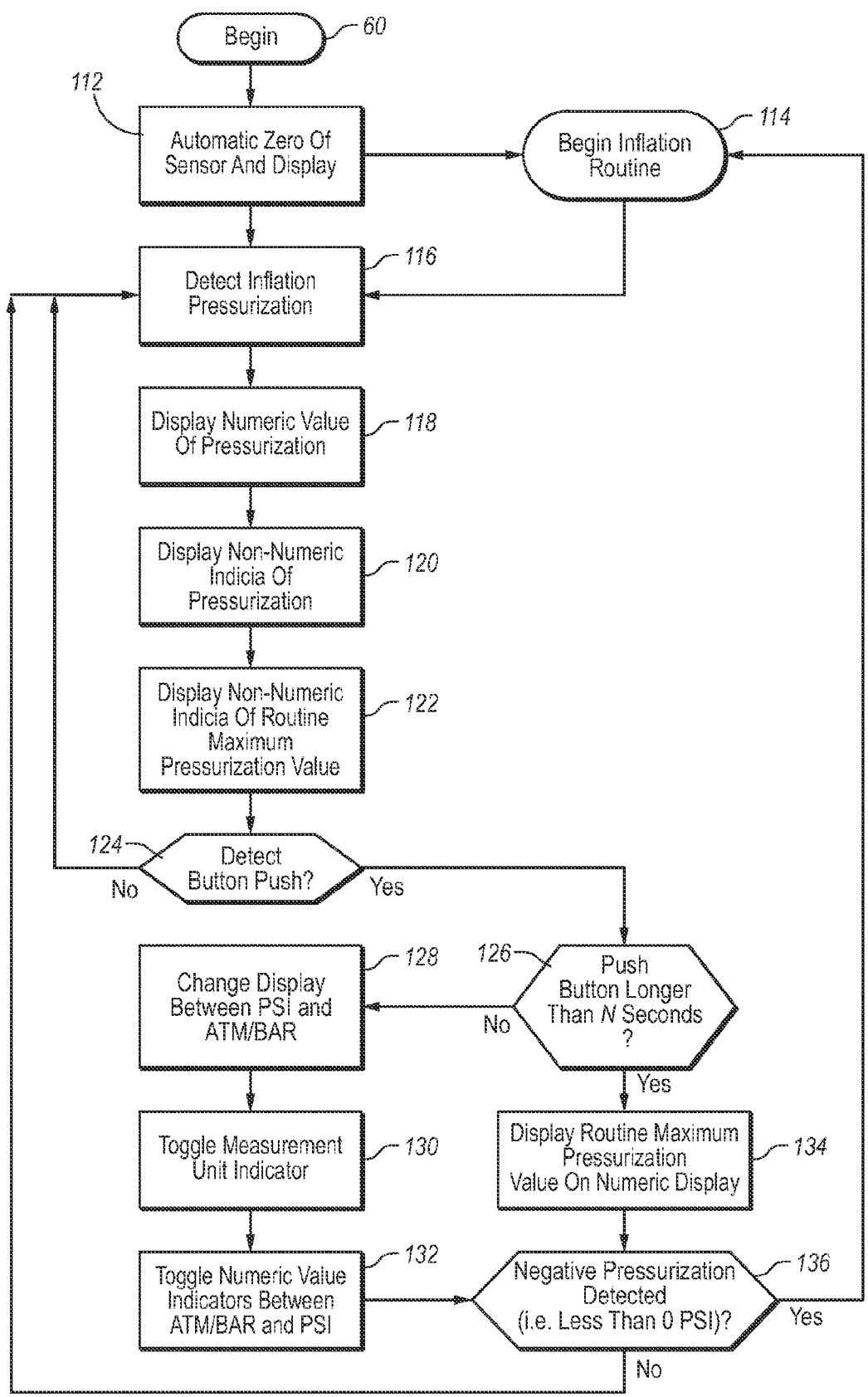
FIG. 6 is a logic flow diagram depicting a method of displaying pressurization information utilizing numeric and non-numeric indicia according to an alternative embodiment of the present invention.

FIG. 6 is a logic flow diagram illustrating a method of detecting pressurization and displaying pressurization information to a user. In the illustrated embodiment, the method begins in a step 60. The system automatically zeros the sensor and/or the display in a step 112. Once the sensor and/or the display are zeroed, an inflation routine is begun in a step 114. Once the inflation routine is begun, a inflation pressurization is detected in a step 116. Once the inflation pressurization is detected in a step 116, the numeric value of the pressurization is displayed in a step 118. Non-numeric indicia of pressurization are then displayed in a step 120. Once the non-numeric and numeric indicia of pressurization are displayed, non-numeric indicia of a routine maximum inflation value are displayed in a step 122. Where the current pressurization is the same as the maximum pressurization experienced during the current pressurization routine, the non-numeric indicia representative of the current pressurization and the routine maximum pressurization value can be the same non-numeric indicia.

It is then determined whether a button of the user interface or other actuation mechanism is pushed or otherwise actuated in a step 124. If no button push is detected, then the method returns to step 116 in which the inflation pressurization is detected. If a button push is detected, then it is determined if the button push is longer than a specified time, such as N seconds in a decision step 126. If the button push is longer than the specified time, the routine maximum pressurization value is displayed on the numeric display in a step 134. According to one embodiment of the present invention, the system is configured to automatically return to displaying current pressurization after a predetermined period of time. According to another embodiment of the present invention, the system returns to displaying current pressurization only after the button is again pushed for the predetermined period of time as discussed with reference to step 126.

Returning to a discussion of whether a button push is longer than a specified time, such as N seconds in a decision step 126, if the button push is not longer than the specified time, the display is changed to display pressurization in an alternative measurement units such as from PSI to ATM/BAR in a step 128. Once the display is changed between measurement units, the measurement unit indicator is toggled to indicate the measurement unit in which the current pressurization is displayed in a step 130. The numeric value indicators are then toggled to provide a numeric value of non-numeric indicia with which they correspond in the correct measurement unit in a step 132. Subsequent to steps 132 and/or steps 134, it is determined whether a negative pressurization is detected (i.e. less than zero psi in a step 136.) In the event that a negative pressurization is detected, a new inflation routine is begun in step 114. in the event that a negative pressurization is not detected, the inflation pressurization is detected in a step 116.

As will be appreciated by those skilled in the art, a variety of types and configurations of methods for detecting pressurizations and displaying pressurizations can be utilized without departing from the scope and spirit of the present invention. For example, according to one embodiment of the present invention, current and representative pressurizations can be displayed utilizing only a non-numeric display. For example, according to one embodiment of the present invention, current and representative pressurizations can be displayed utilizing only a numeric display. According to another embodiment of the present invention, the inflation pressurization can be detected absent a change in pressurization. According to another embodiment of the present invention, the inflation pressurization can automatically be detected at a specified interval such as every $\frac{1}{5}^{th}$ of a second. According to another embodiment, the numeric, non-numeric and representative pressurization information can be updated simultaneously or in any variety of orders.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope. Note that elements recited in means-plus-function format are intended to be construed in accordance with 35 U.S.C. §112 ¶6.

What is claimed is:

1. An inflation syringe configured to allow a medical practitioner to selectively provide a desired amount of inflation pressurization during a medical procedure to inflate a medical instrument, the inflation syringe comprising:

a barrel defining an inner lumen and being configured to hold a desired inflation pressure;

a plunger configured to be received within the inner lumen of the barrel to increase pressurization within the barrel;

a sensor apparatus for sensing inflation pressurization within the barrel; and a display mounted to the exterior of the barrel and configured to link to the sensor apparatus when the display is mounted to the barrel to display the inflation pressurization detected by the sensor apparatus within the barrel, wherein the display includes a numeric indicator which provide a numeric indication of a current inflation pressurization within the barrel and a plurality of discrete non-numeric indicia which are actuated to provide a non-numeric representation of the current inflation pressurization, wherein the non-numeric indicia are actuated in a progressive manner such that non-numeric indicia representing values less than the current inflation pressurization value remain actuated as the pressurization increases and decreases, and wherein the non-numeric indicia simultaneously provide a non-numeric representation of a value that is different from the current inflation pressurization.

2. The inflation syringe of claim 1, wherein the non-numeric indicia provide a visual representation of the inflation pressurization along a range of possible inflation pressures.

3. The inflation syringe of claim 1, wherein the plurality of non-numeric indicia are arranged in an array.

4. The inflation syringe of claim 3, wherein the array includes a first indicium which corresponds with a first pressurization value and a second indicium that corresponds with a second pressurization value.

5. The inflation syringe of claim 2, wherein the non-numeric indicia further provides non-numeric representation of a maximum pressurization within the barrel during the most recent inflation routine.

6. The inflation syringe of claim 2, wherein the non-numeric indicia is arranged in a curvilinear configuration.

7. The inflation syringe of claim 2, wherein the non-numeric indicia is arranged in a linear configuration.

8. The inflation syringe of claim 2, wherein the non-numeric indicia is arranged in a non-linear configuration.

9. The inflation syringe of claim 2, wherein the plurality of non-numeric indicia are analog.

10. The inflation syringe of claim 2, wherein the plurality of non-numeric indicia are digital.

11. A display for use with an inflation syringe configured to allow a medical practitioner to selectively provide a desired amount of inflation pressurization during a medical procedure to inflate a medical instrument, the display comprising:

a housing configured to mount to the exterior of a barrel of the inflation syringe and to couple to a pressure sensing apparatus in fluid communication with the interior of the barrel;

an interface which receives information from the pressure sensing apparatus related to the inflation pressurization within the barrel of the inflation syringe;

a numeric indicator which provides a numeric indication of the inflation pressurization within the barrel; and a plurality of non-numeric indicia which provide a non-numeric representation of the inflation pressurization within the barrel, wherein the plurality of non-numeric indicia are actuated in a progressive manner such that non-numeric indicia representing values less than the current inflation pressurization value remain actuated as the pressurization increases and decreases, wherein, upon completion of an inflation routine, the numeric indicator automatically displays the maximum pressurization value of the completed inflation routine and the plurality of non-numeric indicia automatically provides a non-numeric representation of the same maximum inflation pressurization value.

12. The display of claim 11, wherein the non-numeric indicia simultaneously provide a non-numeric representation of the inflation pressurization within the barrel and a non-numeric representation of the maximum inflation pressurization within the barrel during the most recently completed inflation routine.

13. The display of claim 11, wherein upon completion of an inflation routine the numeric indicator automatically display the maximum pressurization value of the completed inflation routine, and wherein the plurality of non-numeric indicia automatically provides a non-numeric representation of the same maximum inflation pressurization value.

14. The display of claim 11, wherein the interface further comprises:

a processor to process the information related to the inflation pressurization within the barrel of the syringe; and a display module coupled to the processor, wherein the display module displays the inflation pressurization information, and wherein the display module comprises the numeric indicia and non-numeric indicia.

15. The display of claim 14, wherein the housing comprises a base and a hood configured to couple together around the processor and display module, wherein the base is configured to attach to the barrel of the syringe to secure the display to the syringe.

16. A display for use with an inflation syringe configured to allow a medical practitioner to selectively provide a desired amount of inflation pressurization during a medical procedure to inflate a medical instrument, the display comprising:

a housing configured to mount to the exterior of a barrel of the inflation syringe and to couple to a pressure sensing apparatus in fluid communication with the interior of the barrel;

and a plurality of discrete non-numeric indicia each corresponding to an inflation pressurization value, wherein the plurality of non-numeric indicia are consecutively positioned in a single array to provide an indication of the current inflation pressurization, wherein the plurality of non-numeric indicia are actuated in a progressive manner such that non-numeric indicia representing values less than the current inflation pressurization value remain actuated as the current inflation pressurization increases and decreases, and wherein the plurality of non-numeric indicia are configured to simultaneously provide a non-numeric representation of the current inflation pressurization value and a second inflation pressurization value that is different from the current inflation pressurization value.

17. The display of claim 16, further comprising a numeric indicia to display precise inflation pressurization information.

18. An inflation syringe configured to allow a medical practitioner to selectively provide a desired amount of inflation pressurization during a medical procedure to inflate a medical instrument, the inflation syringe comprising:

a barrel defining an inner lumen and being configured to hold a desired inflation pressure;

a plunger configured to be received within the inner lumen of the barrel to increase the pressurization with the barrel;

a sensor apparatus for sensing the inflation pressurization within the barrel; and a display mounted to the exterior of the barrel and configured to link to the sensor apparatus when the display is mounted to the barrel to display the inflation pressurization detected by the sensor apparatus within the barrel, the display having a numeric indicator to provide a numeric indication of a current inflation pressurization within the barrel and a plurality of non-numeric indicia which are actuated in a progressive manner to provide a non-numeric representation of the inflation pressurization, such that non-numeric indicia representing values less than the current inflation pressurization value remain actuated as the pressurization increases and decreases, wherein the plurality of non-numeric indicia are configured to simultaneously provide an indication of a representative inflation value that is different from the current inflation pressurization of the barrel of the inflation syringe, wherein, upon completion of an inflation routine, the numeric indicator automatically displays the representative inflation value that is different and the plurality of non-numeric indicia automatically provides a non-numeric representation of the same maximum inflation pressurization value.

19. The inflation syringe of claim 18, wherein the representative inflation value that is different is a maximum inflation value during the most recently completed inflation routine.

20. The inflation syringe of claim 18, wherein the representative inflation value is a user-defined target inflation value.

21. The inflation syringe of claim 18, wherein the indication of the representative inflation value is provided by actuating one of the plurality of a non-numeric indicia differently than non-numeric indicia actuated to indicate the current inflation pressurization.

22. The inflation syringe of claim 21, wherein the one of the plurality of a non-numeric indicia is actuated differently by displaying a different color.

23. The inflation syringe of claim 18, wherein non-numeric indicia representing values greater than the current inflation pressurization and less than the representative value are not actuated.

24. The inflation syringe of claim 1, wherein the representative inflation value is a maximum inflation value during the most recently completed inflation routine.

25. The inflation syringe of claim 1, wherein the display is releasably mounted to the exterior of the barrel.

26. The display of claim 11, wherein the housing is configured to releasably mount to the exterior of the barrel.

* * * * *